United States Patent [19]
Popov et al.

[11] Patent Number: 5,702,412
[45] Date of Patent: Dec. 30, 1997

US005702412A

[54] METHOD AND DEVICES FOR PERFORMING VASCULAR ANASTOMOSIS

[75] Inventors: Alexander Popov, Los Angeles, Calif.; Peter Barath, Hinsdale, Ill.

[73] Assignee: Cedars-Sinai Medical Center, Los Angeles, Calif.

[21] Appl. No.: 538,575

[22] Filed: Oct. 3, 1995

[51] Int. Cl.⁶ ............................................. A61B 17/32
[52] U.S. Cl. ........................... 606/159; 606/153; 606/170; 606/180
[58] Field of Search .................. 606/1, 159, 150, 606/152, 153, 170, 180; 607/126, 127, 131; 128/899

[56] References Cited

U.S. PATENT DOCUMENTS

| | | |
|---|---|---|
| 4,018,228 | 4/1977 | Goosen . |
| 4,210,132 | 7/1980 | Perlin . |
| 4,216,776 | 8/1980 | Downie et al. ............... 606/184 |
| 4,368,736 | 1/1983 | Kaster . |
| 4,745,919 | 5/1988 | Bundy et al. ............... 606/159 |
| 4,809,713 | 3/1989 | Grayzel . |
| 4,929,240 | 5/1990 | Kirsch et al. . |
| 4,930,674 | 6/1990 | Barak . |
| 4,983,176 | 1/1991 | Cushman et al. . |
| 5,015,249 | 5/1991 | Nakao et al. . |
| 5,041,082 | 8/1991 | Shiber ............... 606/159 |
| 5,047,039 | 9/1991 | Avant et al. . |
| 5,047,040 | 9/1991 | Simpson et al. . |
| 5,078,723 | 1/1992 | Dance et al. ............... 606/159 |
| 5,170,925 | 12/1992 | Madden et al. . |
| 5,174,276 | 12/1992 | Crockard . |
| 5,188,638 | 2/1993 | Tzakis . |
| 5,220,928 | 6/1993 | Oddsen et al. . |
| 5,234,447 | 8/1993 | Kaster et al. . |
| 5,258,008 | 11/1993 | Wilk . |
| 5,330,486 | 7/1994 | Wilk . |
| 5,366,462 | 11/1994 | Kaster et al. . |
| 5,376,095 | 12/1994 | Ortiz . |

FOREIGN PATENT DOCUMENTS

| | | |
|---|---|---|
| 0373927 | 6/1990 | European Pat. Off. ............ 606/159 |
| 422689 | 4/1991 | European Pat. Off. . |
| 0 672 386 A1 | 9/1995 | European Pat. Off. . |
| 44 08 746 A1 | 9/1995 | Germany . |
| 1635966 | 3/1991 | Russian Federation . |
| WO 8100668 | 3/1981 | WIPO . |
| WO 95/17127 | 6/1995 | WIPO . |

*Primary Examiner*—William Lewis
*Attorney, Agent, or Firm*—Pretty, Schroeder & Poplawski

[57] ABSTRACT

A method and devices are provided for performing end-to-side anastomoses between the severed end of a first hollow organ and the side-wall of a second hollow organ utilizing transluminal approach with endoscopic assistance. In particular, the method utilizes a catheter, having a selectively operable cutter, which is introduced into the first hollow organ until the distal end of the catheter is substantially adjacent to the severed end of the first hollow organ. The severed end of the first hollow organ is positioned in proximity to the site for anastomoses on the side wall of the second hollow organ and the severed end is secured in sealing engagement with the side-wall, thereby defining a region of securement on the side wall of the second hollow organ. The severed end of the first hollow organ is preferably secured to the side wall of the second hollow organ by activating a corkscrew element in the catheter to penetrate the side-wall of the second hollow organ and hold the severed end of the first hollow organ in mating engagement with the side-wall of the second hollow organ. A plurality of clips can be applied to the seam between the first hollow organ and the second hollow organ. Alternatively, the first and second hollow organs can be secured by suturing. The cutter is then activated to remove a portion of the side-wall of the second hollow organ, thereby creating an opening within the region of securement and establishing the anastomosis.

35 Claims, 5 Drawing Sheets

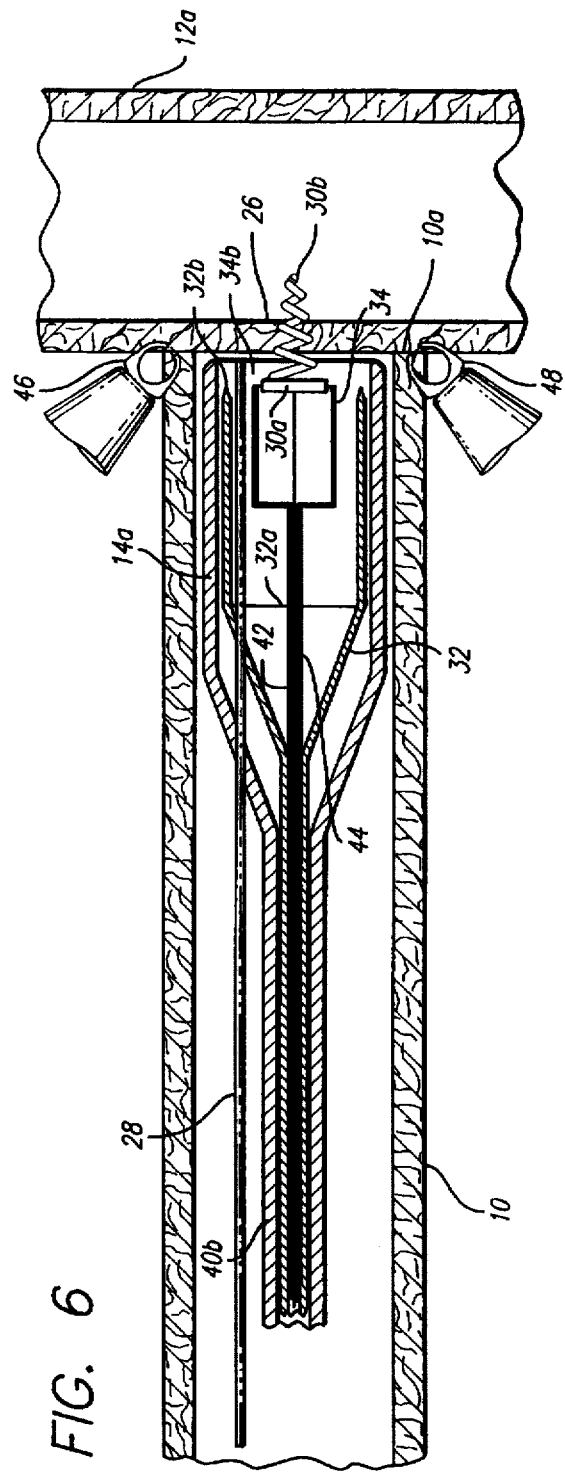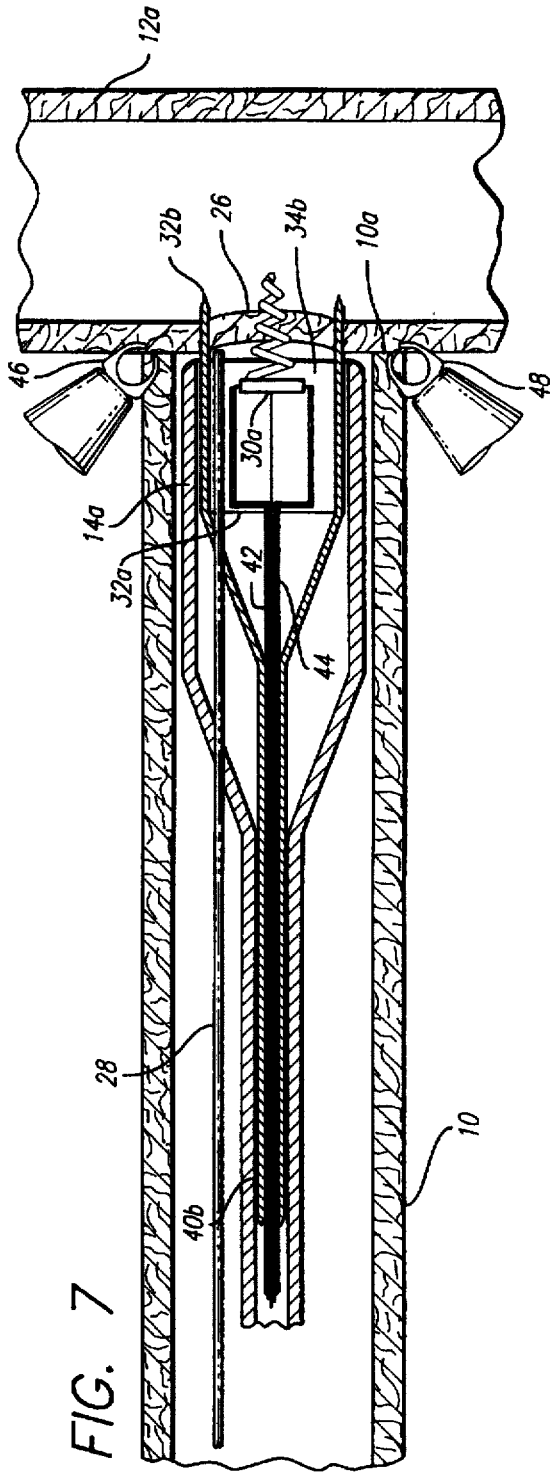

METHOD AND DEVICES FOR PERFORMING VASCULAR ANASTOMOSIS

These methods and devices find particular utility in coronary bypass surgery, including, in particular, where the first hollow organ is the left internal memory artery (LIMA) and the second hollow organ is the left anterior descending coronary artery (LAD).

BACKGROUND OF THE INVENTION

This invention relates generally to the field of surgery and, more particularly, to a method and devices for performing anastomoses. More specifically, the present invention relates to a method and devices for performing end-to-side vascular anastomoses utilizing transluminal approach with endoscopic assistance, including, performing end-to-side anastomoses between intact thoracic or abdominal arteries and diseased coronary arteries.

Anastomosis is the union or joinder of one hollow or tubular organ to another so that the interior of the organs communicate with one another. There are generally two types of anastomosis: end-to-end and end-to-side. In an end-to-end anastomosis, the severed end of a first hollow organ is coupled, usually by suturing or stapling, to the severed end of a second hollow organ. In an end-to-side anastomosis, however, the severed end of a first hollow organ is connected around an opening cut into the side of a second hollow organ.

Typically, anastomoses are performed between airways, blood vessels, bowels, and urogenital lumens. The procedure for connecting blood vessels is referred to as vascular anastomosis. One of the best known surgical procedures utilizing vascular anastomoses is the coronary bypass. In the context of coronary artery disease, the flow of oxygenated blood to the myocardium of the heart is inhibited by a stenosis or obstruction in the coronary artery. This flow can be improved by providing a coronary artery bypass graft ("CABG") between the aorta and a point in the coronary artery distal to stenosis. Typically, a section of vein from the leg is removed and attached at one end to the aorta and at the other end to the coronary artery utilizing end-to-side anastomoses. Such grafts are known as saphenous coronary artery bypass grafts. Alternatively, synthetic grafts can be utilized to effect the bypass.

While the typical coronary bypass procedure favorably affects the incidence and severity of angina in patients with coronary artery disease, a variety of risks are associated with such procedures. Among them are mortality, myocardial infarction, postoperative bleeding, cerebrovascular accident, arrhythmias, wound or other infection, aortic dissection and limb ischemia. Furthermore, the vein grafts deteriorate over time, thereby resulting in the recurrence of angina, myocardial infarction and death. In addition, the costs of such procedures are relatively high and the patient recovery relatively long.

In an attempt to overcome such problems, a number of alternative approaches have been developed. For example, artery to artery bypass procedures have been utilized in which an arterial source of oxygenated blood-such as the left internal mammary artery ("LIMA"), right internal mammary artery ("RIMA"), or right internal thoracic artery ("RITA") —is severed and anastomosed to the obstructed coronary artery distally to the stenosis or occlusion. More recently, other arteries have been used in such procedures, including the inferior epigastric arteries and gastroepiploic arteries. In general, artery to artery bypass procedures have demonstrated a better patency rate as compared with autologous vein or synthetic grafts.

While vascular anastomoses can be effective, and sometimes life-saving procedures, traditionally available techniques have been associated with a number of complications. For example, conventional techniques for performing vascular anastomoses generally require an extensive incision in the patient's body. Such operations are traumatic to the patient, involve a lengthy recovery, and a relatively high risk of infection or other complications.

In the context of coronary bypass surgery, for example, the bypass graft or artery-to-artery procedure is traditionally performed using an open chest procedure. In particular, each procedure involves the necessity of a formal 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Furthermore, such procedures leave an unattractive scar and are painful to the patient. Most patients are out of work for a long period after such an operation and have restricted movement for several weeks. Such surgery often carries additional complications such as instability of the sternum, post-operative bleeding and mediastinal infection. Cutting through layers of the patients tissue may also severely traumatize the tissue and upset the patients emotional equilibrium. Above all, open procedures are associated with long recuperation times.

Due to the risks attendant to such procedures, there has been a need to develop procedures which minimize invasion of the patient's body tissue and resulting trauma. In this regard, limited open chest techniques have been developed in which the coronary bypass is carried out using an abdominal (subxyphoid) approach or, alternatively, a "Chamberlain" incision (an approximately 8 cm incision at the sternocostal junction), thereby lessening the operating area and the associated complication rate. While the risks attendant to such procedures are generally lower than their open chest counterparts, there is still a need for a minimally invasive surgical technique. Nevertheless, each of these techniques is thoracotomic, requiring an incision to be made in the chest wall through which conventional surgical instruments are introduced to perform conventional coronary bypass surgery.

In order to reduce the risk of patient mortality, infection, and other complications associated with surgical techniques, it is advantageous and desirable to utilize endoscopic and thoracoscopic surgical techniques. Such procedures usually involve the use of surgical trocars which are used to puncture the abdomen or chest, thereby facilitating access to a body cavity through the cannula and a relatively small opening in the patient's body. Typically, such trocars have a diameter of about 3 mm to 15 mm. Surgical instruments and other devices such as fiber optic cameras can be inserted into the body cavity through the cannula. Advantageously, the use of trocars minimizes the trauma associated with many surgical procedures.

When traditional vascular anastomoses are performed, it is desirable to effect a suitable leak-proof connection between organs. Typically, such connections are established using suturing techniques. It is significant to note, however, that suturing of vascular structures is a tedious and time consuming process. Furthermore, these suturing techniques are not readily adapted for to endoscopic techniques where the surgeon's freedom of access and movement are more limited. Thus, there is a need for an alternative to these suturing techniques that would expedite the procedure, and a further need for an alternative that can be readily adapted for endoscopic use.

Various stapling techniques are known for providing anastomotic connections between organs, such as in intestinal and colorectal anastomoses. Due to the size of these devices, however, they are not easily adapted for use with vascular organs or endoscopic techniques. Furthermore, such techniques typically require penetration of the organ wall. Thus, due to the increased likelihood of clotting associated with penetration of the interior of the vascular wall, these techniques have not found ready application to the vascular system.

Recently, a surgical procedure and surgical clip have been developed which are intended to facilitate the anastomoses of vascular structures. In this technique, the vascular tissues are approximated, partially everted, and then clipped by applying the arms of the surgical clip over the everted tissue and securing the clip so as to hold the tissue together without penetrating the interior wall of the vessel. Nevertheless, in order to properly utilize these clips, the tissues should be everted. It would be desirable if such clipping devices could be adapted for endoscopic use. Further, it would be desirable to eliminate the need for everting the tissue prior to application of the clips in order to facilitate endoscopic assisted anastomoses.

It should, therefore, be appreciated that there is a definite need for a method and devices for performing vascular anastomoses which minimize the risk of infection, trauma, and other complications associated with conventional surgery, and, in particular, a need for a device which can be utilized in conjunction with an endoscopic technique for vascular anastomoses.

SUMMARY OF THE INVENTION

The present invention, which addresses this need, resides in a method and devices for performing vascular anastomoses in a manner that tends to minimize the risk of infection, trauma, and other complications associated with conventional surgery. In this regard, the present invention combines transluminal and endoscopic techniques.

In the preferred embodiment, the present invention relates to a nonthoracotomic, minimally invasive method and devices for establishing end-to-side anastomoses between the severed end of a first hollow organ and the side wall of a second hollow organ utilizing transluminal approach with endoscopic assistance. A catheter having a selectively operable cutter adapted to remove a portion of the side-wall of the second hollow organ, is introduced into the first hollow organ until the distal end of the catheter is substantial adjacent to the severed end of the first hollow organ. The severed end is then positioned in proximity to the proposed site for anastomosis of the side-wall of the second hollow organ. The severed end of the first hollow organ is secured in sealing engagement with the side-wall of the second hollow organ, thereby defining a zone of securement. The cutter is activated to remove a portion of the side-wall of the second hollow organ within the zone of securement, thereby establishing the anastomosis.

In more detailed aspects of the invention, the distal end of the catheter is sized and shaped to provide support to the severed end of the first hollow organ so that a plurality of clips may be applied to the seam between the severed end of the first hollow organ and the side-wall of the second hollow organ without the necessity of everting the edges. Alternatively, the severed end of the first hollow organ can be secured to the side wall of the second hollow organ by suturing with endoscopic assistance.

In still more detailed aspects of the invention, the catheter can be equipped with a corkscrew element adapted to penetrate hold the side wall of the second hollow organ in mating engagement with the severed end of the first hollow organ. A clipping device is described whereby a plurality of clips can be simultaneously applied to the seam between the severed end of the first hollow organ and the side wall of the second hollow organ. In the preferred embodiment, the clips can be applied simultaneously and expeditiously.

The method and devices of the present invention find particular application for performing vascular anastomoses, including, in particular, coronary bypass between an arterial source and an obstructed coronary artery. In particular, the method and devices of the present invention find particular application in establishing an anastomoses between the severed end of the left internal memory artery ("LIMA") and the side wall of the left anterior descending coronary artery ("LAD").

BRIEF DESCRIPTION OF THE DRAWINGS

FIG. 6 a cross-sectional view illustrating the placement of the clips shown in FIG. 5 thereby securing the severed end of the arterial source to the side-wall of the coronary artery.

FIG. 7 is a cross-sectional view illustrating activation of the cutter to remove a portion of the side-wall of the coronary artery within the area of securement of the severed end of the arterial source and the coronary artery.

DESCRIPTION OF THE PREFERRED EMBODIMENT

In preparation for the surgical procedure of the present invention, the patient is placed on the operating table in a supine position, and general anaesthesia administered. A double-lumen endotracheal tube is selectively intubated using conventional methods, thereby permitting the left lung to be deflated. The patient is then placed in a lateral decubitus position on his right side. Next, based upon the pathology and anatomy of the patient, the surgeon identifies a suitable position for insertion of a Beress insufflation needle or other suitable needle. Typically, this needle will be inserted between the fifth or sixth intercostal space along the anterior axillary line and into the region between the parietal pleura and the pericardium. The parietal pleura and pericardium are then separated by conventional gas dissection, and the Beress needle is removed.

Figure 1:
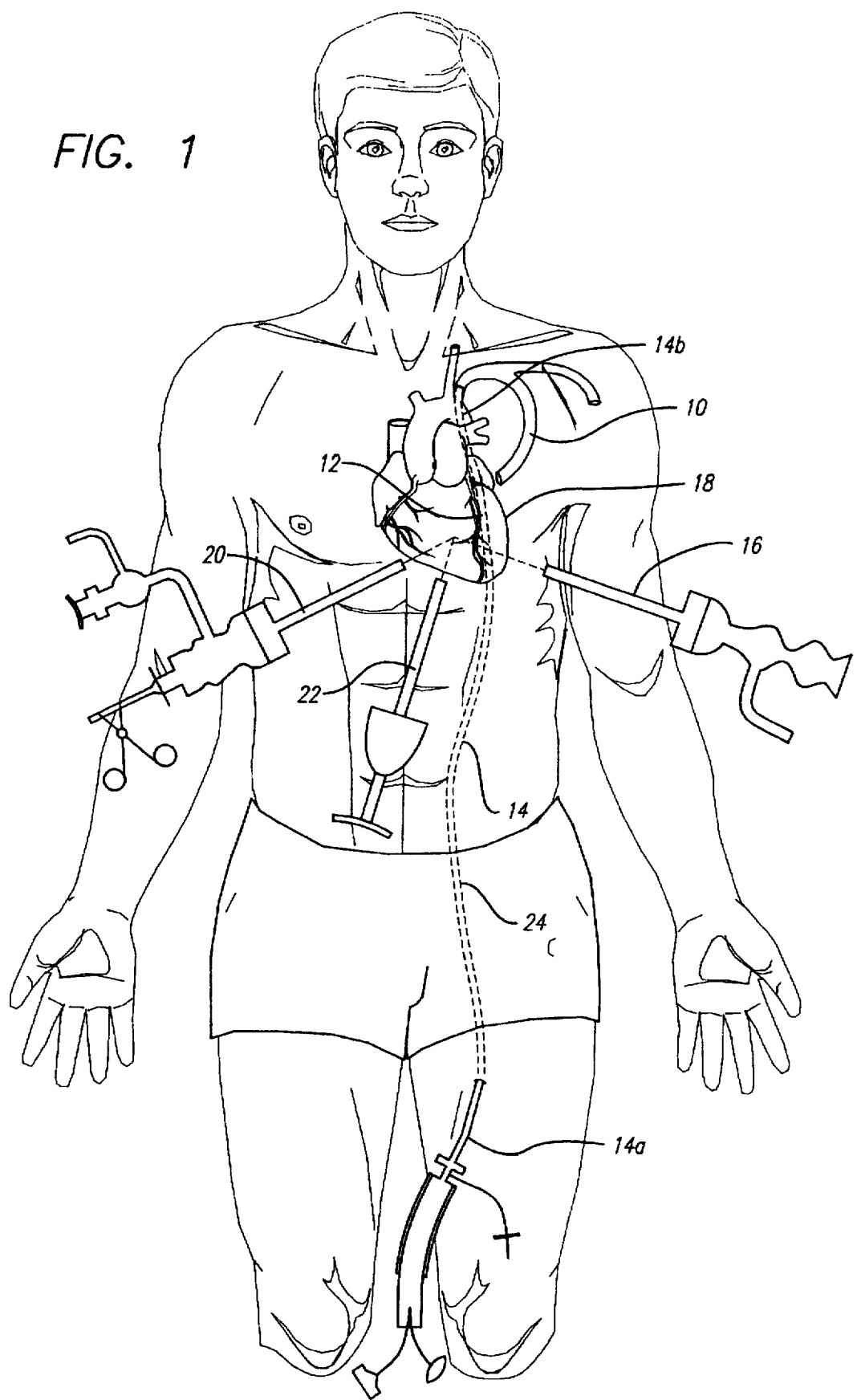
FIG. 1 is a schematic perspective view of a patient in undergoing a coronary bypass procedure, showing the placement of three surgical trocars and the transluminal approach of a cutter catheter in accordance with the present invention.

With reference now to the exemplary drawings, and particularly to FIG. 1, there is shown a schematic perspective view of a patient undergoing an artery-to-artery coronary bypass procedure in accordance with the present invention in which an end-to-side vascular anastomosis is established between the severed end of the left internal mammary artery ("LIMA") 10 and the side-wall of the left anterior descending coronary artery ("LAD") 12 distally to the site of a stenosis. A cutter catheter 14 in accordance with the present invention is disposed within the LIMA 10. The proximal end 14a of the cutter catheter 14 is located outside of the patient and the distal end 14b is located near the severed end of the LIMA.

A first trocar (not shown) and trocar port 16 each having a diameter of approximately 8 to 12 mm and, preferably, 10 mm, are introduced into the thoracic cavity along the same path traveled by the Beress insufflation needle. The trocar is then removed and a conventional endoscopic telescope (not shown) is introduced through the trocar port 16 into the thoracic cavity. This telescope is used to directly visualize the thoracic cavity and obtain a left lateral view of the heart 18.

Based upon (a) direct visualization using the endoscopic telescope; (b) the location of the arterial source (in this case, the LIMA 10), the heart 18 and the coronary artery (in this case, the LAD 12); and (c) the anatomy and pathology of the patient, the surgeon determines a suitable location for insertion of a second trocar (not shown) and trocar port 20 and a third trocar (not shown) and trocar port 22. Typically, however, the second trocar and trocar port 20 will be inserted through the intercostal wall and into the thoracic cavity, and the third trocar and trocar port 22 through the subxyphoid space. Additional trocars or other instruments can be inserted as necessary. Often, it will be advantageous to insert a fourth trocar and trocar port for introducing a clipping or suturing device into the thoracic cavity.

Prior to performing the anastomosis, it is also desirable to visualize the coronary artery using conventional angiographic techniques. Typically, the surgeon will already have an angiogram of the affected coronary artery available as a result of the earlier diagnosis of the necessity for the coronary bypass. Similarly, it is desirable to use conventional angiographic techniques to visualize the arterial source. Thus, in the preferred embodiment, the LIMA is visualized using a conventional angiographic LIMA catheter. As a result, as shown in FIG. 1, a standard angiographic LIMA guiding catheter will have been introduced into the femoral artery 24 and advanced under angiographic control through the aorta and left subclavian artery to the ostium of the LIMA 10.

Under the guidance of the endoscopic telescope, conventional endoscopic instruments are used to isolate the LIMA 10 from surrounding tissue and the chest wall. A number of considerations are taken into account in determining the site for severing the LIMA 10. Using the angiographic and direct visualization, the surgeon can determine a desirable proposed site for severing which will provide a suitable length of artery with a diameter that closely matches that of the coronary artery. A maximum length of the LIMA 10 can be obtained by severing the LIMA 10 at its distal end near the diaphragm. In preparation for severing, blood flow to the side branches of the LIMA 10 is interrupted by clipping or cauterizing the branches of the LIMA proximally of the proposed site for severing. Blood flow through the LIMA 10 is interrupted by applying a first clip on the proximal side of the proposed site for severing and a second clip on the distal side of the proposed site for severing. The LIMA 10 is then severed using conventional endoscopic techniques, thereby creating a proximal severed end and a distal severed end.

Using conventional endoscopic techniques, the parietal pleura is dissected and the pericardial sac is opened. The endoscopic telescope can be used to visualize the LAD 12 while the LAD 12 is then isolated endoscopically from the surrounding tissue proximally and distally of the proposed site for anastomosis.

Figure 2:
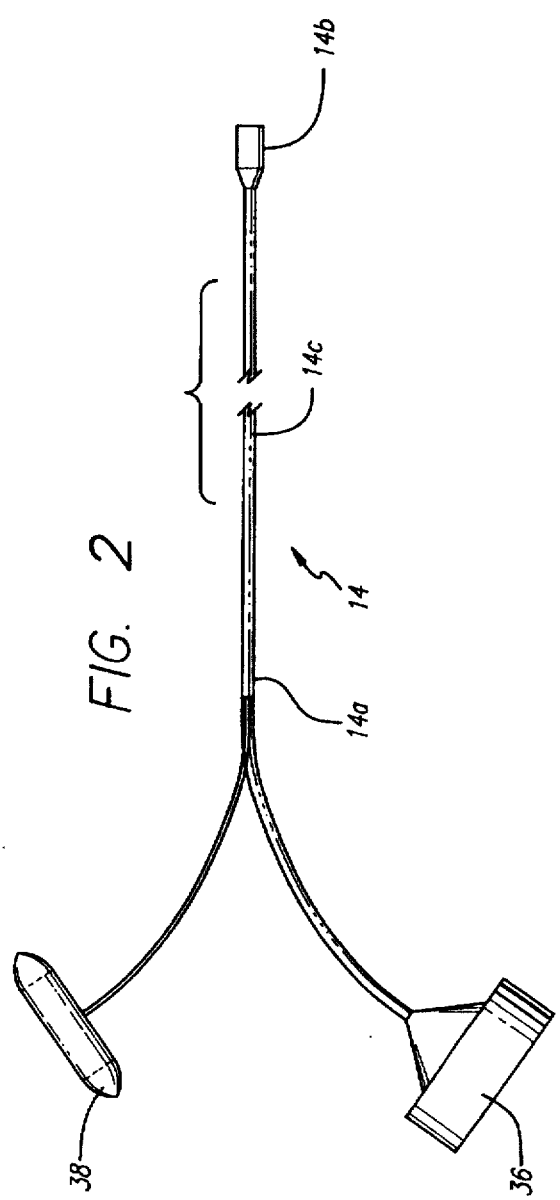
FIG. 2 is a elevational view of a cutter catheter adapted for use in the coronary bypass procedure shown in FIG. 1.

With reference now to FIG. 2, there is shown a cutter catheter 14 for use in performing vascular anastomoses which comprises a substantially cylindrical, elongate body 14c having a proximal end 14a and a distal end 14b. The body portion 14c of the cutter catheter 14 is adapted for introduction into and through the angiographic LIMA guiding catheter (not shown) and into and through the LIMA 10.

Figure 3:
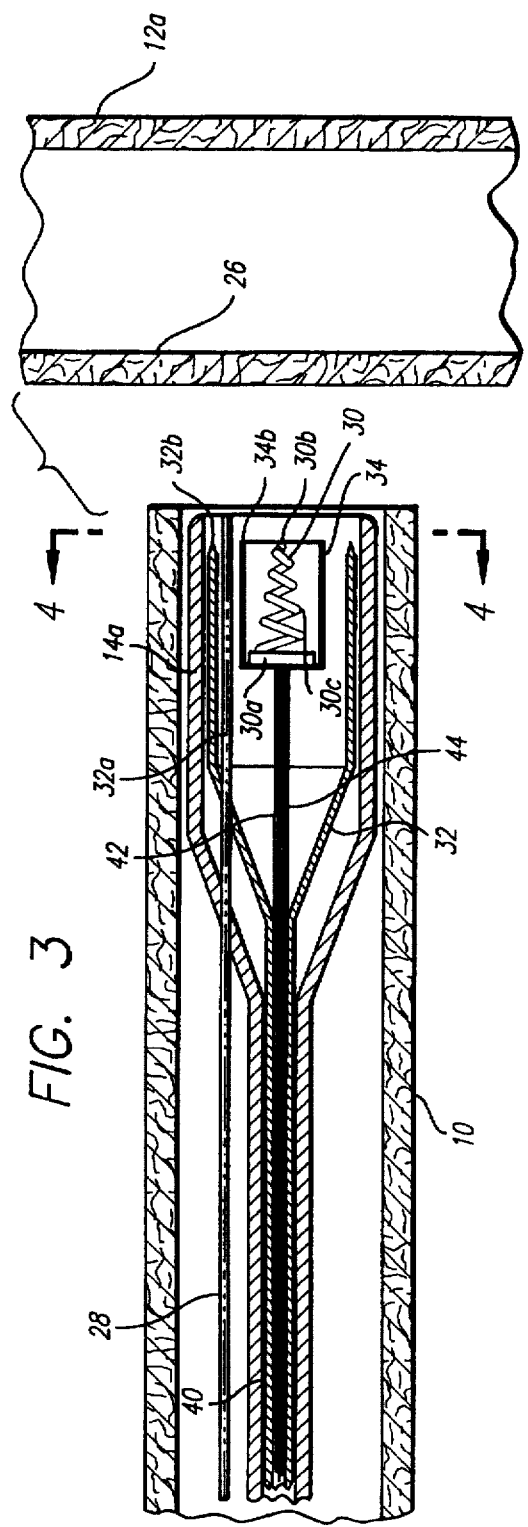
FIG. 3 is a cross-sectional view of the distal end of the cutter catheter shown in FIG. 2 disposed in proximity to the severed end of an arterial source and showing a corkscrew element and a cutter in proximity of the proposed site for anastomosis on the side-wall of a coronary artery.

As shown in FIG. 3, the proximal severed end 10a of the LIMA 10 is then placed in proximity to the proposed site for anastomosis 12a on the side wall 10a of the LAD 12 using endoscopic assistance. A cutter catheter 14 in accordance with the present invention has been inserted through the guiding catheter and into the LIMA 10 using a conventional guide wire 28 under angiographic control. The cutter catheter 14 includes a proximal end 14a which remains outside of the patient and a distal end 14b which is disposed within the LIMA 10 near the proposed site for severing the LIMA.

As discussed above, insertion of the cutter catheter 14 is accomplished with the assistance of a conventional guide wire 28. The guide wire 28 and cutter catheter 14 are first inserted into the opening in the proximal end of the angiographic LIMA guiding catheter. The guide wire is then advanced through the angiographic LIMA guiding catheter to the ostium of the LIMA 10, then further advanced through the LIMA 10 to the clip at the proximal severed end. The cutter catheter 14 is then loaded over the guide wire and the distal end 14b of the cutter catheter 14 is positioned in proximity to the proximal severed end 10a of the LIMA 10. A ligation (not shown) is applied around the exterior of the LIMA 10 and the distal end 14b of the cutter catheter 14 near the proximal severed end 10a in order to hold the cutter catheter 14 in place and also to restrict the flow of fluid once the clip is removed from the proximal severed end 10a. After this ligature is established, the first clip is removed from the proximal severed end 10a.

Once these initial preparations have been undertaken, the more detailed aspects of the surgical procedure are initiated. To this end, FIGS. 3–6 depict different stages in the establishment of an end-to-side anastomotic connection in accordance with the present invention. FIG. 3 is a cross-sectional view of the distal end 14b of the cutter catheter 14 shown in FIG. 2 disposed in proximity to the proximal severed end 10a of the LIMA 10 and showing a corkscrew element 30 and a cutter 32 contained within the distal end 14b of the body 14c of the cutter catheter 14 in proximity to the proximal severed end 10a of the LIMA 10. The proximal severed end 10a of the LIMA 10 is located in a position near the proposed site for anastomosis 26 on the side-wall 12a of the LAD 12.

As shown in FIG. 3, the distal end 14b of the cutter catheter 14 defines a substantially cylindrical hollow bore 14d. The cutter 32 is disposed within this hollow bore 14d and adapted to extend along and rotate about the longitudinal axis of the cutter catheter 14 beyond the distal end 14b thereby contacting and removing a portion of the side-wall 12a of the LAD 12 at the proposed site for anastomosis 26. Furthermore, the distal end also includes a corkscrew element 30 disposed within the interior of a substantially cylindrical housing 34. The corkscrew element 30 and cylindrical housing 34 are adapted to extend along and rotate about the longitudinal axis of the cutter catheter 14. The corkscrew element 30 may be operated independently from the cylindrical housing 34.

Figure 4:
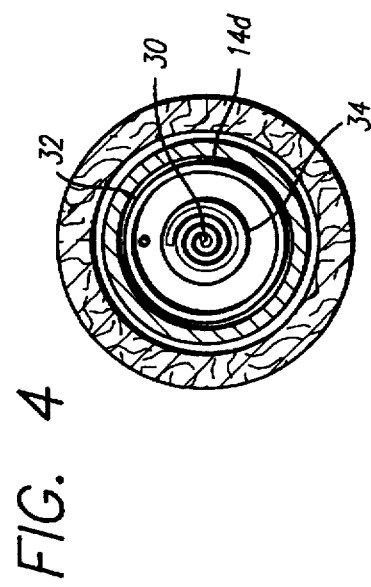
FIG. 4 is a radial cross-sectional view taken along line 4—4 of FIG. 3, showing the distal end of the cutter catheter and the coaxial relationship of the corkscrew element and the cutter.
Figure 5:
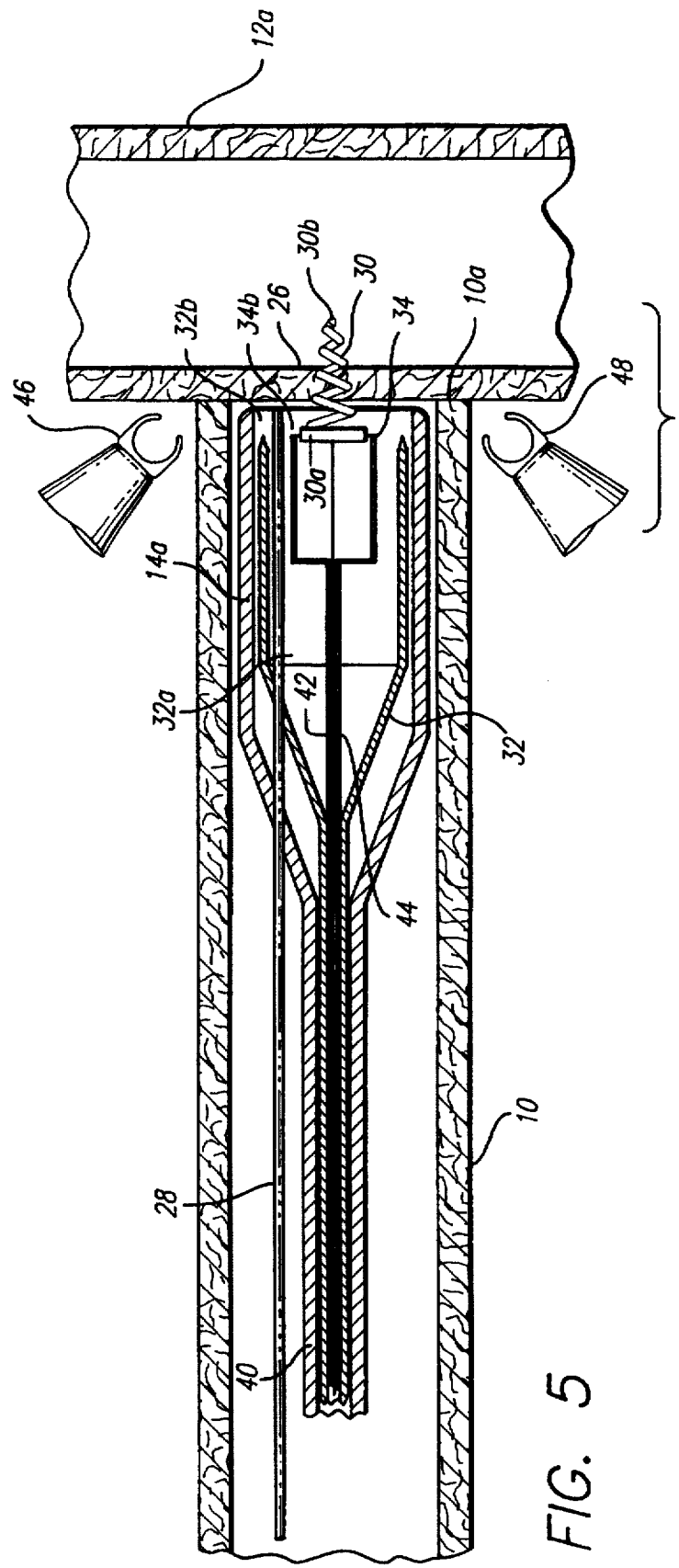
FIG. 5 a cross-sectional view illustrating the position of the clips at the junction between the severed end of the arterial source and the side-wall of the coronary artery after the arterial source has been secured in mating engagement with the side-wall by activation of the corkscrew element.

Referring now to FIG. 4, there is shown a radial cross-sectional view taken along line 4—4 of FIG. 3 of the distal end 14b of the cutter catheter 14 disposed within the LIMA 10 and placed in proximity to the LAD 12. The cutter 32 is disposed in substantially coaxial relationship with the substantially cylindrical hollow bore 14d near the distal end 14b of the cutter catheter 14, and the corkscrew element 30 and cylindrical housing 34, in turn, are also in substantially coaxial relationship to the bore 14d of the cutter catheter 14.

In the preferred embodiment, the cutter 32 is a substantially cylindrical hollow body having proximal end 32a and a distal end 32b. The distal end 32b of the cutter 32 includes a sharpened edge or cutting surface adapted to remove a substantially circular portion of the side-wall 12a of the LAD 12. Preferably, the length of the cutter 32 is approximately one-half of the width of the LAD 12 at the proposed site for anastomosis 26, in order to prevent injury to the opposite wall of the LAD 12 when the cutter 32 is extended into the interior of the LAD 12.

Movement of the cutter 32 is selectively controlled using a first controller handle 36 located at the proximal end 14b of the cutter catheter 14. (See, FIG. 2.) The first control handle 36 and cutter 32 are attached to opposite ends of a first control conduit 40 disposed within the body 14c of the cutter catheter 14. By changing the position of the first control handle 36 relative to the proximal end 14a of the cutter catheter 14, the first control conduit 40 is moved longitudinally within the body 14c of the cutter catheter 14 thereby extending the cutter 32. In addition, the first control handle 36 can be rotated thereby rotating the first control conduit 40 and in turn the cutter 32 about the longitudinal axis of the cutter catheter 14. Thus, by combining longitudinal movement and rotation of the first control hand 40, the cutter 32 can be simultaneously extended and rotated, thereby contacting the cutting surface 32b of the cutter 32 with the side-wall 12a of the LAD 12 and extending the cutting surface through the side wall 12a of the LAD 12.

In the preferred embodiment, the cutter catheter 14 also includes a corkscrew element 30, disposed within the cylindrical housing 34, which includes a base 30a, pointed tip 30b adapted to puncture the side-wall 12a of the LAD 12 and a spiral body 30c adapted to be threaded through and engage the side-wall 12a of the LAD 12. Movement of the corkscrew element 30 is selectively controlled using a second controller handle 38 located at the proximal end 14a of the cutter catheter 14. (See, FIG. 2) The second control handle 38 and corkscrew element 30 are attached to opposite ends of a second control wire 42. The control wire is disposed within a control wire conduit 44. By changing the position of the second control handle 38 relative to the proximal end 14a of the cutter catheter 14, the second control wire 42 is moved longitudinally within the control wire conduit body 44 of the cutter catheter 14 thereby extending the corkscrew element 30. Similarly, by changing the position of the control wire conduit 44 relative to the proximal end 14a, the cylindrical housing 34 is moved longitudinally withing the distal end 14b of the cutter catheter 14. In addition, the second control handle 38 can be rotated thereby rotating the second control wire 42 and in turn the corkscrew element 30 about the longitudinal axis of the cutter catheter 14. Thus, by combining longitudinal movement and rotation of the second control handle 38, the corkscrew element 30 can be simultaneously extended and rotated, thereby contacting the pointed tip 30b of the corkscrew element 30 with the side-wall 12a of the LAD 12 and threading the spiral body 30c through the side wall 12a of the LAD 12.

Preferably, the length of the corkscrew element 30 is approximately one-half of the width of the LAD, in order to prevent injury to the part of the LAD arterial wall opposite to the point of anastomoses when the corkscrew element is threaded through the side-wall of the LAD.

Referring to FIGS. 3 and 5–7, several cross-sectional views are shown illustrating the securement of the proximal severed end 10a of the LIMA 10 to the side-wall 12a of the LAD 12. First, by moving the control wire conduit 44, the cylindrical housing 34 and corkscrew element 30 are moved longitudinally within the distal end 14b of the cutter catheter 14 thereby placing the distal end 34b of the cylindrical housing 34 and tip 30b of the corkscrew element 30 in proximity to the proposed site for anastomosis 26 on the side-wall 12a of the LAD 12.

Optionally, the surgeon can aspirate the control wire conduit 44 at the proximal end 14a of the cutter catheter 14, thereby generating an area of negative pressure within the cylindrical housing 34 at the distal end 14b of the cutter catheter 14 and adhering the side-wall 12a of the LAD 12 in mating engagement with the severed end 10a of the LIMA 10 at the proposed site for anastomosis 26. Thereafter, by combining longitudinal movement and rotation of the second control handle 38, the corkscrew element 30 is extended and rotated so that the pointed tip 30b of the corkscrew element 30 pierces the side-wall 12a of the LAD 12 and the spiral body 30b is threaded through the side wall 12 of the LAD 12 thereby further fixing the proximal severed end 10a in mating engagement with the proposed site for anastomosis 26 on the side wall 12a of the LAD 12. (See FIG. 5.)

Referring to FIGS. 6–7, after the proximal severed end 10a of the LIMA 10 is brought into mating engagement with the site for anastomosis 26 on the side wall 12a of the LAD 12, removable snares (not shown) are applied to the LAD 12 proximally and distally to the proposed site for anastomosis 26 and the LIMA 10 and LAD 12 are secured in sealing engagement using clips 46 and 48 applied along the seam between the proximal severed end 10a of the LIMA 10 and the side wall 12a of the LAD 12, thereby defining a zone of securement between the LIMA 10 and the LAD 12. In particular, it is believed that the surgical clip and applier described in U.S. Pat. No. 4,929,240 to Kirsch et al. (incorporated herein by reference) will find ready application in the present method. Alternatively, the anastomosis can be established by other suitable means such as suturing. In the preferred embodiment, however, the distal end 14b of the cutter catheter 14 is sized and shaped to provide support to the severed end 10a of the LIMA 10, so that the clips may be applied without the necessity of everting the tissue at the proposed site for anastomosis 26.

Finally, as shown in FIG. 7, once the LIMA 10 and LAD 12 are secured in sealing engagement, the first controller handle 36 is activated to extend and rotate the cutter 32, thereby removing a substantially circular portion of the side-wall 12a of the LAD 12 within the area of securement of the proximal severed end 10 of the LIMA 10 and secured by the corkscrew element 30. Thus, the anastomosis is established.

After the side-wall 12 is cut, the first and second control handles are moved thereby retracting the cutter 32 and corkscrew element 30 and the removed portion of the side wall 12a of the LAD 12 within the hollow bore 14d at the distal end 14b of the cutter catheter 14.

Figure 8:
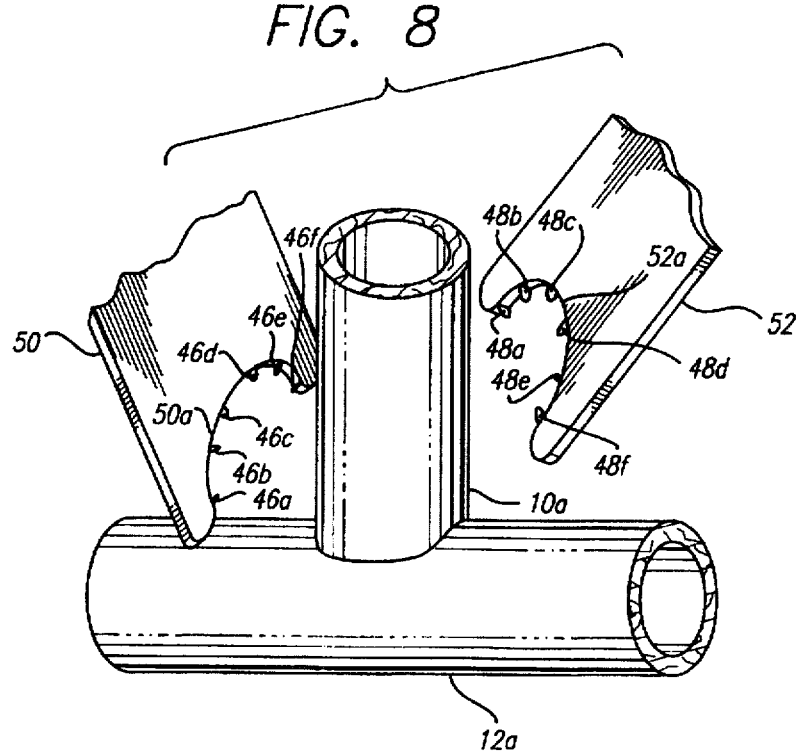
FIG. 8 is a perspective view showing the placement of two clipping devices adapted to simultaneously apply a plurality of clips to secure the severed end of the arterial source in sealing engagement with the side wall of the coronary artery.
Figure 9:
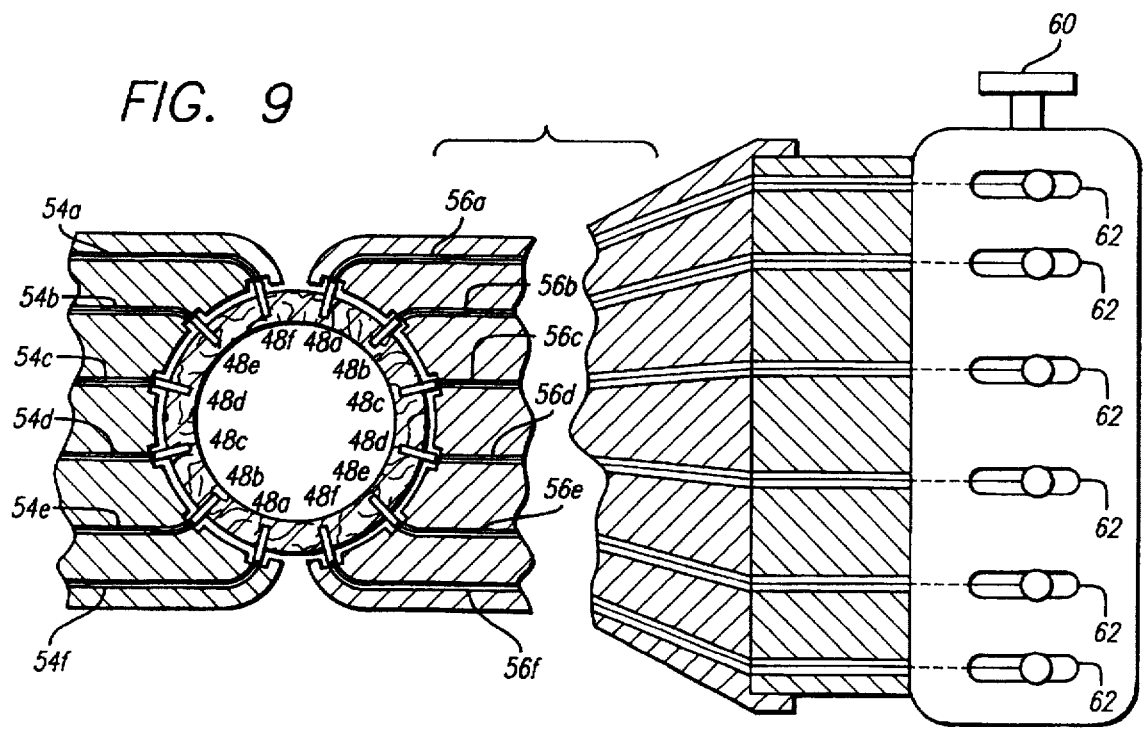
FIG. 9 is a cross-sectional view of the clipping devices shown in FIG. 8 showing the controller utilized in connection with placement and adjustment of a plurality of independently controllable clips thereby securing the severed end of the arterial source to the sidewall of the coronary artery.

As shown in FIGS. 8–9, in the preferred embodiment, the LIMA 10 and LAD 12 are secured in sealing engagement utilizing two clip appliers 50 and 52 that are introduced through the trocar ports 20 and 22 to the proposed site for anastomosis 26. The arcuate edges 50a and 52a of each clip applier are placed along the seam between the proximal severed end 10a of the LIMA 10 and the side wall 12a of the LAD 12. Each clipping device, 50 and 52, includes a plurality of individually operable clips, 46a–f and 48a–f, along its respective arcuate edge, 50a and 52a. Each clip is connected by a clip control wire 54a–f and 56a–f to a controller 58, only one of which is shown. Preferably, the clip appliers 50 and 52 are positioned around the circumference of the seam between the severed end 10a of the LIMA 10 and the side-wall 12a of the LAD 12 whereby each of the clips 46a–f and 48a–f can be simultaneously activated, by activating control button 60, to secure the distal end 10a of the LIMA 10 to the side-wall 12a of the LAD 12. Thereafter, each clip may be individually adjusted utilizing the individual clip controls 62a–f connected to the clip control wires 56a–f.

As discussed above, in the preferred embodiment, the cutter catheter 14 will be sized and shaped to provide support to the LAD as the clips are applied. Thus, it is expected that the clips can be applied without first cutting the side-wall of 12a of the LAD 12 and everting the proximal severed end 10a of the LIMA 10 and the severed edge of the LAD 12. Furthermore, where the surgeon is able to apply the clips simultaneously and thereby expeditiously establish the anastomosis, it is contemplated that the procedure can be performed on the beating heart.

Where the anastomosis is to be performed on the beating heart, it is advantageous to slow the heart to 30–40 beats per minute by the intravenous administration of beta blockers. This slowing of the heart will facilitate securement of the LIMA to the LAD without the necessity of inducing cardiac arrest. Even where it is contemplated that the procedure will be performed on the beating heart, prophylactic measures should be taken so that femoral to femoral cardiopulmonary bypass can be initiated if necessary. Where the method is to be applied to surgery on an arrested heart, preparations should be made for femoral to femoral cardiopulmonary bypass.

Once the anastomosis is established, the ligature around the cutter catheter 14 is released and the cutter catheter 14 is removed along with the portion of the side-wall 12a removed from the LAD 12 and engaged by the corkscrew element 30. The snares can then be removed from the LAD 12. Once an angiographic check of the anastomosis is performed, the guide wire and guiding catheter can be removed. The pericardial sac is then closed and the endoscopic equipment and trocars removed. Finally, any remaining air is aspirated from the thoracic cavity and all incisions closed.

Although a particular form of the invention has been illustrated and described, it will be appreciated by those skilled in the art that various modifications can be made without departing from the spirit and scope of the invention. Accordingly, the scope of the present invention is not to be limited by the particular embodiments above, but is to be defined only by the following claims.

I claim:

1. A catheter for performing an end-to-side anastomosis between a severed end of a first hollow organ and a side-wall of a second hollow organ of a patient, comprising:
   an elongated body having proximal and distal ends and adapted for introduction into and through the first hollow organ; and
   a selectively operable cutter disposed within the body and having a cutting surface at the distal end which is configured to remove a portion of a side-wall of the second hollow organ.

2. The catheter of claim 1, wherein the distal end of the catheter defines a bore having an aperture in the distal end of the catheter and the cutter is disposed within the bore.

3. The catheter of claim 1, wherein the cutter includes:
   an elongated cutter body disposed axially within the elongated catheter body and extendable along a longitudinal axis of the elongated catheter body; and
   a cutting element associated with the elongated cutter body and configured for engagement with the second hollow organ.

4. The catheter of claim 3, wherein the catheter further includes a controller adapted to control the cutter.

5. The catheter of claim 1, wherein the catheter further includes a corkscrew element adapted to engage the side-wall of the second hollow organ whereby the severed end of the first hollow organ is held in mating engagement with the side-wall of the second hollow organ.

6. The catheter of claim 5, wherein the catheter further includes a controller adapted to control the corkscrew element.

7. The catheter of claim 6, wherein the controller includes a control wire disposed within the elongated body and movable along the longitudinal axis of the body of the catheter, the control wire further being connected to a control handle at the proximal end of the catheter and to the at the distal end of the catheter.

8. The catheter of claim 5, wherein the proximate end of the catheter includes a first controller adapted to control the corkscrew element and a second controller adapted to control the cutter.

9. A method for establishing an end-to-side anastomosis between a severed end of a first hollow organ and a side-wall of a second hollow organ, the method comprising:
   (a) introducing a catheter, having proximal and distal ends, into the first hollow organ and passing the catheter through the first organ until the distal end of the catheter is substantially adjacent to the severed end of the first hollow organ, the catheter having a selectively operable cutter adapted to remove a portion of the side-wall of the second hollow organ;
   (b) positioning the severed end of the first hollow organ in proximity with the site for anastomosis of the second hollow organ;
   (c) securing the severed end of the first hollow organ in sealing engagement with the side-wall of the second hollow organ, thereby defining a region of securement on a side-wall of the second hollow organ; and (d) activating the cutter to remove a portion of a side-wall of the second hollow organ thereby creating an opening within the region of securement defined by the engagement of the severed end of the first hollow organ with the side-wall of the second hollow organ.

10. The method of claim 9, wherein the first and second hollow organs are both vascular lumens.

11. The method of claim 9, wherein the first hollow organ is the left internal mammary artery and the second hollow organ is a coronary artery.

12. The method of claim 11, wherein the catheter is first introduced into and through the femoral artery.

13. The method of claim 11, wherein the catheter is first introduced into and through the brachial artery.

14. The method of claim 9, wherein the method further includes:

generating an area of negative pressure in the interior of the catheter near the severed end, thereby engaging the side-wall of the coronary artery with the severed end of the Left Interior Mammary Artery.

15. The method of claim 9, wherein the securing of the severed end of the first hollow organ in sealing engagement with the side-wall of the second hollow organ, includes stapling the first hollow organ to the sidewall of the second hollow organ.

16. The method of claim 9, wherein the securing of the severed end of the first hollow organ in sealing engagement with the side-wall of the second hollow organ, includes suturing the first hollow organ to the sidewall of the second hollow organ.

17. A method for performing end-to-side anastomosis between a severed end of a first hollow organ and a side-wall of a second hollow organ, the method comprising:

(a) introducing a catheter, having proximal and distal ends, into the first hollow organ and passing the catheter through the first organ until the distal end of the catheter is substantially adjacent to the severed end of the first hollow organ, the catheter having a corkscrew element and a selectively operable cutter adapted to remove a portion of the side-wall of the second hollow organ;

(b) positioning the severed end of the first hollow organ in proximity with the site for anastomosis of the second hollow organ;

(c) activating the corkscrew element whereby corkscrew element penetrates the side wall of the severed hollow organ and the severed end of the first hollow organ is held in mating relationship with the second hollow organ;

(d) securing the severed end of the first hollow organ in sealing engagement with the side-wall of the second hollow organ, thereby defining a region of securement on a side-wall of the second hollow organ; and (e) activating the cutter to remove a portion of a side-wall of the second hollow organ thereby creating an opening within a region of securement defined by the engagement of the severed end of the first hollow organ with the side-wall of the second hollow organ.

18. The method of claim 17, wherein the first and second hollow organs are both vascular lumens.

19. The method of claim 17, wherein the first hollow organ is the left internal mammary artery and the second hollow organ is a coronary artery.

20. The method of claim 17, wherein the catheter is first introduced into and through the femoral artery.

21. The method of claim 17, wherein the catheter is first introduced into and through the brachial artery.

22. The method of claim 17, wherein the method further includes:

generating an area of negative pressure in the interior of the catheter near the severed end, thereby engaging the side-wall of the coronary artery with the severed end of the LIMA.

23. The method of claim 17, wherein the securing of the severed end of the first hollow organ in sealing engagement with the side-wall of the second hollow organ, includes stapling the first hollow organ to the side-wall of the second hollow organ.

24. The method of claim 17, wherein the stage of securing the severed end of the first hollow organ in sealing engagement with the side-wall of the second hollow organ, includes suturing the first hollow organ to the side-wall of the second hollow organ.

25. A method for performing a coronary bypass by establishing an end-to-side anastomosis between an arterial source of oxygenated blood and a coronary artery having a stenosis, the method comprising:

(a) introducing a catheter, having proximal and distal ends, into the arterial source and passing the catheter through the arterial source until the distal end of the catheter is substantially adjacent to the severed end of the arterial source, the catheter having a selectively operable cutter adapted to remove a portion of the side-wall of the coronary artery;

(b) severing the arterial source;

(c) positioning the severed end of the arterial source in proximity with the site for anastomosis of the coronary artery;

(d) securing the severed end of the first hollow organ in sealing engagement with the side-wall of the second hollow organ, thereby defining a region of securement on a side-wall of the second hollow organ;

(e) activating the cutter to remove a portion of a side-wall of the coronary artery thereby creating an opening within the region of securement defined by the engagement of the severed end of the arterial source with the side-wall of the coronary artery.

26. The method of claim 25, wherein the first and second hollow organs are both vascular lumens.

27. The method of claim 25, wherein the first hollow organ is the left internal mammary artery and the second hollow organ is a coronary artery.

28. The method of claim 25, wherein the catheter is first introduced into and through the femoral artery.

29. The method of claim 25, wherein the catheter is first introduced into and through the brachial artery.

30. The method of claim 25, wherein the method further includes:

generating an area of negative pressure in the interior of the catheter near the severed end, thereby engaging the side-wall of the coronary artery with the severed end of the Left Interior Mammary Artery.

31. The method of claim 25, wherein the stage of securing the severed end of the first hollow organ in sealing engagement with the side-wall of the second hollow organ, includes stapling the first hollow organ to the side-wall of the second hollow organ.

32. The method of claim 25, wherein the stage of securing the severed end of the first hollow organ in sealing engagement with the side-wall of the second hollow organ, includes suturing the first hollow organ to the side-wall of the second hollow organ.

33. A method for performing coronary bypass by effecting an end-to-side anastomoses between a arterial source of oxygenated blood and a coronary artery, the method comprising:

(a) introducing a plurality of trocar ports through the intercostal spaces of a patient;

(b) performing gas dissection of the thoracic cavity;

(c) isolating an arterial source of oxygenated blood;

(d) severing the arterial source;

(e) introducing a catheter, having proximal and distal ends, into the arterial source and passing the catheter through the arterial source until the distal end of the catheter is substantially adjacent to the severed end of the arterial source, the catheter having a corkscrew element adapted to penetrate and secure the side wall of the coronary artery, and a selectively operable cutter adapted to remove a portion of the side-wall of the coronary artery;

(f) performing endoscopic dissection of the parietal pleura;

(g) opening the pericardial sac;

(h) isolating the coronary artery proximally and distally to the site for anastomosis;

(i) placing the severed end of the arterial source in proximity to the site of anastomosis;

(j) activating the corkscrew element whereby the severed end of the arterial source is held in mating relationship with the coronary artery;

(k) securing the severed end of the arterial source in sealing engagement with the side wall of the coronary artery;

(l) activating the cutter whereby a portion of the side wall of the coronary artery engaged by the corkscrew element is removed;

(m) removing the cutter catheter and the portion of the side wall engaged by the corkscrew element;

(n) closing the pericardial sac;

(o) removing the trocar ports; and (p) evacuating the thoracic cavity.

34. The method of claim 33, wherein the stage of securing the severed end of the first hollow organ in sealing engagement with the side-wall of the coronary artery, includes stapling the first hollow organ to the side-wall of the second hollow organ.

35. The method of claim 33, wherein the stage of securing the severed end of the first hollow organ in sealing engagement with the side-wall of the coronary artery, includes suturing the first hollow organ to the side-wall of the second hollow organ.

* * * * *